United States Patent [19]

Artes et al.

[11] 4,400,528
[45] Aug. 23, 1983

[54] PROCESS FOR METHYLATING SILICON COMPOUNDS

[75] Inventors: Reinhold Artes; Volker Frey; Werner Graf; Norbert Zeller, all of Burghausen, Fed. Rep. of Germany

[73] Assignee: Wacker-Chemie GmbH, Munich, Fed. Rep. of Germany

[21] Appl. No.: 372,499

[22] Filed: Apr. 28, 1982

[30] Foreign Application Priority Data

May 15, 1981 [DE] Fed. Rep. of Germany ....... 3119462

[51] Int. Cl.$^3$ .............................................. C07F 7/08
[52] U.S. Cl. ................................. 556/430; 556/435
[58] Field of Search ................................ 556/430, 435

[56] References Cited

U.S. PATENT DOCUMENTS

| | | | |
|---|---|---|---|
| 2,381,000 | 8/1945 | Patnode et al. | 556/435 |
| 2,507,519 | 5/1950 | Goodwin | 556/435 X |
| 2,886,582 | 5/1959 | Kautsky et al. | 556/430 |
| 2,908,698 | 10/1959 | Kuriyagawa et al. | 556/430 |
| 4,158,010 | 6/1979 | Graf et al. | 556/430 UX |

FOREIGN PATENT DOCUMENTS 53-149933 12/1978 Japan ................................ 556/430

*Primary Examiner*—Paul F. Shaver

[57] ABSTRACT

A process for methylating silicon compounds containing halogen and at least 2 silicon atoms and optionally carbon and hydrogen atoms as the only atoms in the molecule, which comprises reacting a silicon compound containing halogen and at least two silicon atoms per molecule, such as hexachlorodisilane or 1,1,2,2-tetrachloro-1,2-dimethyldisilane or mixtures of such silanes with tetramethylsilane in the presence of at least one organoaluminum compound having the general formula $$R_a AlY_{3-a'}$$

where R represents the same or different alkyl radicals having from 1 to 4 carbon atoms, Y represents halogen, hydrogen or hydrocarbon radicals having from 1 to 10 carbon atoms which are bonded to the aluminum atom via oxygen and which are free of aliphatic multiple bonds, and a is 1, 2 or 3, or an in situ formed compound obtained from the reaction of such aluminum compound, with at least one other reactant present in the reaction mixture, at least one silane of the general formula $$R_b{}^1H_cSiCl_{4-b-c}$$

and hydrogen halide, where $R^1$ represents the same or different hydrocarbon radicals which are free of aliphatic multiple bonds and have from 1 to 10 carbon atoms, b is 0, 1, 2 or 3, and c is 1, 2 or 3, with the proviso that the sum of b+c may not exceed 4.

7 Claims, No Drawings

PROCESS FOR METHYLATING SILICON COMPOUNDS

The present invention relates to methylated silicon compounds and more particularly to a process for methylating silicon compounds containing halogen atoms and at least two silicon atoms per molecule.

BACKGROUND OF THE INVENTION

It is known that silicon compounds containing at least two silicon atoms, halogen atoms and optionally carbon and hydrogen atoms as the only atoms in the molecule can be methylated using the Grignard process, i.e., by incorporating methyl groups into such silicon compound, in order to increase the proportion of methyl groups. This process is described by Makoto Kumada et al in the Journal of Organic Chemistry, Vol. 21 (1956), pages 1264 to 1268.

In contrast to the Grignard process for methylating silicon compounds, the proces of the present invention employs a compound as the source for the methyl groups which is readily available and is easier to handle than the Grignard compounds. In addition, the process of the present invention avoids the formation of inorganic salts which are associated with the Grignard-type process.

A process similar to the present process for methylating organochlorosilanes containing only one silicon atom per molecule is described in U.S. Pat. No. 4,158,010 to Graf et al.

It is known that the redistribution of SiC-bonded methyl groups does not affect silicon atoms which are linked together by at least one methylene group; however, the ≡SiSi≡ linkage is much more sensitive than the ≡SiC linkage. Therefore, it is surprising that the redistribution of SiC-bonded methyl groups does not substantially affect the ≡Si Si≡ linkage. (B. W. Noll, "Chemie und Technologie der Silicone":, 2nd edition, pages 300 to 301). Consequently, the methylation of silicon compounds containing at least two silicon atoms, halogen atoms and optionally carbon and hydrogen atoms as the only atoms in the molecule was not an obvious development in view of the art.

Therefore, it is an object of the present invention to provide methylated silicon compounds. Another object of the present invention is to provide a process for methylating silicon compounds. Still another object of the present invention is to provide a process for methylating silicon compounds having at least two silicon atoms, halogen atoms and optionally carbon and hydrogen atoms as the only atoms in the molecule. A further object of the present invention is to provide a process for methylating silicon compounds in which the compound containing the methyl groups for methylating the silicon compounds is readily available.

SUMMARY OF THE INVENTION

The foregoing objects and others which are apparent from the following description are accomplished in accordance with this invention, generally speaking, by providing a process for methylating silicon compounds which comprises reacting a silicon compound having at least two silicon atoms, halogen atoms and optionally carbon and hydrogen atoms as the only atoms in the molecule, with a tetramethylsilane, at least one silane of the formula

and
a hydrogen halide in the presence of an organoaluminum compound having the general formula

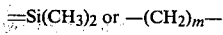

or an in situ produced compound obtained from the reaction of the organoaluminum compound with at least one of the reactants present in the reaction mixture, where R is an alkyl radical having from 1 to 4 carbon atoms, $R^1$ is a hydrocarbon radical having from 1 to 10 carbon atoms which is free of aliphatic multiple bonds, Y is selected from the group consisting of hydrogen, halogen and hydrocarbon radicals having from 1 to 10 carbon atoms which are free of aliphatic unsaturation and are bonded to the aluminum atom via oxygen, a is 1, 2 or 3, b is 0, 1, 2 or 3 and c is 1, 2 or 3, with the proviso that the sum of b+c may not exceed 4.

DETAILED DESCRIPTION OF THE INVENTION

The organosilicon compounds used in the process of this invention, which contain at least two silicon atoms and halogen atoms as well as optionally carbon and hydrogen atoms as the only atoms in the molecule, are preferably those having the general formula $$Cl_{3-d}R_d^1SiQ_eSiR_d^1Cl_{3-d},$$

where $R^1$ is the same as above, and Q represents a group selected from the formula $$=Si(CH_3)_2 \text{ or } -(CH_2)_m-$$

where m is 1 to 10, d is 0, 1 or 2, the specific values of the two d(s) being the same or different, and e is 0 or 1.

Examples of hydrocarbon radicals represented by $R^1$ or hydrocarbon radicals which may form part of Y are alkyl radicals, such as the methyl, ethyl, n-propyl, iso-propyl, n-butyl, sec-butyl and 2-ethylhexyl radicals, as well as decyl radicals; cycloalkyl radicals such as the cyclohexyl radial, aryl radicals, such as the phenyl radical; aralkyl radicals such as the benzyl radical; and alkaryl radicals such as the tolyl radicals.

Specific examples of organosilicon compounds which may be used in the process of this invention and which contain at least two silicon atoms per molecule, halogen atoms as well as, optionally, carbon and hydrogen atoms, as the only atoms in the molecule are the following:

Hexachlorodisilane
1,1,2,2-tetrachloro-1,2-dimethyldisilane
1,2,2-trichloro-1,1,2-trimethyldisilane
1,2-dichloro-1,1,2,2-tetramethyldisilane
1,1,3,3-tetrachloro-1,2,2,3-tetramethyltrisilane
1,2-bis-(trichlorosilyl)-ethane
1-trichlorosilyl-2-methyldichlorosilylethane
1,6-bis-(trichlorosilyl)-hexane.

It is, of course, possible to use mixtures of at least two such compounds, for example, a mixture of from 60 to 70 percent by weight of 1,1,2,2-tetrachloro-1,2-dimethyldisilane and from 30 to 40 percent by weight of 1,2,2-trichloro-1, 1,2-trimethyldisilane.

It is preferred that tetramethylsilane be used in an amount of from 1 to 1.5 moles per gram atom of halogen in the silicon compound which consists of at least 2 silicon atoms and halogen atoms as well as, optionally, carbon and hydrogen atoms, as the only atoms in the molecule.

During the addition of the other reactants used in the process of this invention, the tetramethylsilane may be mixed with an aliphatic hydrocarbon containing from 4 to 10 carbon atoms and which may contain either aliphatic multiple bonds or be free of such multiple bonds.

The examples of hydrocarbon radicals represented by $R^1$, as well as the hydrocarbon radicals which may constitute a part of Y and which have from 1 to 4 carbon atoms, are equally applicable also to hydrocarbon radicals represented by R. An additional example of a hydrocarbon radical represented by R and of a hydrocarbon radical represented by Y which is bonded to the aluminum atom via oxygen is the tert-butyl radical.

Because of its availability, chlorine is the preferred halogen represented by Y. Other halogen atoms represented by Y also include fluorine, bromine or iodine atoms.

Individual examples of organoaluminum compounds which may be used in the process of this invention are the following:
Ethylaluminum sesquichloride
Ethylaluminum dichloride
Trimethylaluminum
Methylaluminum sesquichloride
Diethylaluminum chloride
Tri-n-propylaluminum
n-propylaluminum dichloride
Di-n-butylaluminum hydride
Ethylaluminum sesquiethoxide.

Preferred organoaluminum compounds are those having a boiling point in excess of 150° C. at 1 bar (absolute). Because of its availability, ethylaluminum sesquichloride is the preferred organoaluminum compound. Mixtures of various organo-aluminum compounds may of course be used in the process of this invention.

It is known that organoaluminum compounds may, for example, readily react with hydrogen halide. Therefore, is intended that aluminum compounds formed in situ from the reaction of such organoaluminum compounds with at least one of the reaction components be included in the definition of the organoaluminum compounds illustrated by the formula.

The organoaluminum compound of the general formula $$R_a AlY_{3-a}$$

is preferably used in an amount of from 0.1 to 10 percent by weight, based on the weight of the silicon compound which consists of at least 2 silicon atoms, halogen as well as optionally carbon and hydrogen atoms as the only atoms in the molecule.

Good results are obtained with as little as 0.1 percent by weight, based on the weight of the silicon compound which consists of at least 2 silicon atoms and halogen atoms and, optionally, carbon and hydrogen atoms as the only atoms in the molecule.

Nevertheless, it is preferred that from 0.5 to 6 percent by weight of such an organosilicon compound be present, based on the weight of the silicon compound which comprises at least 2 silicon atoms, halogen and optionally carbon and hydrogen atoms as the only atoms in the molecule.

Specific examples of silanes having the general formula $$R_{b'}^1 H_c SiCl_{4-b-c}$$

are silane, methyldichlorosilane, dimethylchlorosilane, monochlorosilane and trichlorosilane.

It is preferred that silanes having Si-bonded hydrogen be used in an amount of from 0.5 to 15 percent by weight and especially in amounts of from 2 to 6 percent by weight, based on the total weight of the silicon compound containing at least 2 silicon atoms and halogen and, optionally, carbon and hydrogen atoms as the only atoms in the molecule.

The hydrogen halide is preferably employed in an amount of from about 0.1 to 10 percent by weight, based on the weight of the silicon compound containing at least 2 silicon atoms and halogen as well as, optionally, carbon and hydrogen atoms as the only atoms in the molecule. Because of its availability, hydrogen chloride is the preferred hydrogen halide. Also, it is possible to use hydrogen fluoride, hydrogen bromide or hydrogen iodide or a mixture of two or more such hydrogen halides instead of hydrogen chloride.

The process of this invention is preferably carried out at room temperature, i.e., at temperatures of from about 20° to 60° C. and under atmospheric pressure, i.e., at approximately 1 bar (absolute). Nevertheless, it is also possible to use higher or lower pressures. If desired, solvents which are inert to the components of the reaction mixture may be used as well.

As far as possible, it is preferred that the process of this invention be conducted under anhydrous conditions.

The aluminum compound can be deactivated by compounds which contain oxygen prior to distilling the mixture obtained in accordance with the process of this invention. Examples of compounds which may be used for deactivating the aluminum compound are monovalent or polyvalent alcohols, preferably monovalent alcohols such as ethanol. Other compounds which may be employed are ketones such as acetone; organopolysiloxanes containing dimethylpolysiloxanes which are liquid at room temperature and which are end-blocked by trimethylsiloxy groups, dimethylpolysiloxanes which are liquid at room temperature and which contain an Si-bonded hydroxyl group in each of its terminal units, and octamethylcyclotetrasiloxane. However, the aluminum compound may be deactivated by complexing with metal chlorides. Any residual, unreacted Si-bonded chlorine atoms may be substituted with methyl groups by using the Grignard process before or after the process has been completed.

Hexamethyldisilanes prepared in accordance with this invention may, for example, be reacted with iodine to form trimethyliodosilane.

In the following examples all percentages are by weight unless otherwise specified.

EXAMPLE 1

About 13 liters of gaseous hydrogen chloride, measured at 20° C. and at 1 bar (abs.) which corresponds to about 1.6 percent based on the weight of the disilane used, is passed at 20° C. over a period of about one hour with agitation and at a pressure of about 1 bar (absolute) through a mixture consisting of 1,260 g of tetramethylsilane having a purity of 94 percent as determined by gas chromatography, and 1,200 g of a liquid which according to gas chromatographic analysis consists of 50 percent 1,1,2,2-tetrachloro-1,2-dimethyldisilane, 40 percent of 1,2,2-trichloro-1,1,2-trimethyldisilane and 10 percent of undetermined constituents, 43 g of ethylaluminum sesquichloride and 44 g of methyldichlorosilane, in a 3-necked flask equipped with a stirrer, a reflux condenser, a thermometer and a gas dispersing tube. The mixture is then heated to boiling under reflux for 8 hours, during which time the temperature of the boiling mixture increases to 54° C. After the contents of the flask have cooled, 25 ml of a trimethylsiloxy endblocked dimethylpolysiloxane which has a viscosity of about 100 mm$^2 \cdot$s$^{-1}$ re added to the contents of the flask, followed by fractionation distillation. About 900 g of a fraction which boils at between 100° and 140° C. at about 1 bar is recovered and analyzed by gas chromatography. The results are shown below:

| | |
|---|---|
| Hexamethyldisilane | 41 percent |
| Chloropentamethyldisilane | 45 percent |
| Dichlorotetramethyldisilane (isomer mixture) | 12 percent |
| 1,2,2-trichloro-1,1,2-trimethyldisilane | 2 percent |

EXAMPLE 2

About 5 liters of gaseous hydrogen chloride measured at 20° C. and at about 1 bar (absolute), corresponding to about 0.83 percent of the weight of the disilane used, is passed over a period of 30 minutes through a mixture containing 2,070 g of a mixture consisting of 40 percent tetramethylsilane and 60 percent saturated and unsaturated aliphatic hydrocarbons, consisting mostly of 2-methylbutane and small amounts of 2-methyl-1-butane and 2,4-dimethylpentane, 17 g of ethylaluminumsesquichloride and 19 g of methyldichlorosilane, in a 3-necked flask which is equipped with a stirrer, a reflux condenser, a thermometer and a gas dispersing tube.

This procedure is carried out under agitation and at 20° C. Within the 30 minute period of time, 750 ml of a liquid, which according to gas chromatographic analysis consists of 50 percent 1,1,2,2-tetrachloro-1,2-dimethyldisilane, 40 percent 1,2,2-trichloro-1,1,2-trimethyldisilane and 10 percent of undetermined constituents is added to the contents of the flask through a dropping funnel mounted on the reflux condenser. The mixture is then heated to boiling under reflux for 12 hours, during which time the temperature of the mixture increases to 40° C. After the flask's contents have cooled, 15 ml of freshly dried acetone is added. The resultant precipitate is removed by filtration, followed by fractionation distillation. A fraction weighing 875 g, which boils at between 100° and 145° C. and at about 1 bar (abs.) is recovered and analyzed by gas chromatography. The results are shown below:

| | |
|---|---|
| Hexamethyldisilane | 21 percent |
| Chloropentamethyldisilane | 65 percent |
| Dichlorotetramethyldisilane (isomer mixture) | 10 percent |
| 1,2,2-trichloro-1,1,2-trimethyldisilane | 4 percent |

What is claimed is:

1. A process for methylating silicon compounds containing halogen and at least two silicon atoms and optionally carbon and hydrogen atoms as the only atoms in the molecule which comprises reacting an organosilicon compound containing halogen and at least two silicon atoms per molecule with tetramethylsilane in the presence of at least one organoaluminum compound of the formula $$R_a AlY_{3-a},$$

at least one silane of the formula $$R_b{}^1 H_c SiCl_{4-b-c}$$

and hydrogen halide, where R is an alkyl radical having from 1 to 4 carbon atoms, R$^1$ is a hydrocarbon radical free of aliphatic multiple bonds having from 1 to 10 carbon atoms, Y is selected from the group consisting of hydrogen, halogen or hydrocarbon radicals which are free of aliphatic multiple bonds and contain from 1 to 10 carbon atoms and are bonded to the aluminum atom via oxygen, a is 1, 2 or 3, b is 0, 1, 2 or 3, c is 1, 2 or 3 with the proviso that the sum of b+c may not exceed 4.

2. The process of claim 1, wherein the reaction is conducted in the presence of an in situ produced reaction product of such an aluminum compound and one of the reactants.

3. The process of claims 1 or 2, wherein the organoaluminum compound is present in an amount of from about 0.1 to about 10 percent by weight, based on the weight of the silicon compound containing halogen and at least two silicon atoms and optionally carbon and hydrogen atoms as the only atoms in the molecule.

4. The process of claims 1 or 2, wherein the silane containing Si-bonded hydrogen is present in an amount of from about 0.5 to about 15 percent by weight, based on the weight of the silicon compound which contains halogen and at least two silicon atoms and optionally carbon and hydrogen atoms as the only atoms in the molecule.

5. The process of claims 1 or 2, wherein hydrogen halide is present in an amount of from about 0.1 to about 10 percent by weight, based on the weight of the silicon compound which contains halogen, and at least two silicon atoms and optionally carbon and hydrogen atoms as the only atoms in the molecule.

6. The process of claim 5, wherein the hydrogen halide is hydrogen chloride.

7. The process of claims 1 or 2, wherein the tetramethylsilane is used in the form of a mixture containing an aliphatic hydrocarbon having from 4 to 10 carbon atoms.

* * * * *